United States Patent [19]
Burnam

[11] Patent Number: 4,975,541
[45] Date of Patent: Dec. 4, 1990

[54] AMINOGLYCOSIDES FOR CONTROLLED DRUG RELEASE

[76] Inventor: Michael H. Burnam, 24372 Rolling View Dr., Hidden Hills, Calif. 91302

[21] Appl. No.: 209,369

[22] Filed: Jun. 21, 1988

[51] Int. Cl.[5] .................... C07H 15/00; C07H 5/00; C07G 3/00; A61K 31/00

[52] U.S. Cl. .................................. 536/13.6; 536/22; 536/17.9; 536/18.7; 536/55.3; 536/55.2; 536/4.1

[58] Field of Search .................. 435/80; 536/13.6, 22, 536/17.9, 18.7, 55.2, 4.1, 55.3; 514/25, 42; 424/450

[56] References Cited

U.S. PATENT DOCUMENTS

| | | | |
|---|---|---|---|
| 3,091,572 | 5/1963 | Luedemann et al. | 536/13.6 |
| 3,136,704 | 6/1964 | Charney | 435/80 |
| 4,746,675 | 5/1988 | Makino et al. | 514/423 |
| 4,844,904 | 7/1989 | Hamaguchi et al. | 424/450 |

*Primary Examiner*—Ronald W. Griffin
*Assistant Examiner*—Everett White

[57] ABSTRACT

The invention disclosed provides a method for preparing spherical-like encapsulated aminoglycosides which may be administered orally to a patient, and which retain antibacterial properties without significant degradation stomachically. The present invention also provides spherical-like encapsulated aminoglycosides and a method for introducing aminoglycosides into a patient by oral ingestion without significant degradation of bactericidal properties.

5 Claims, No Drawings

AMINOGLYCOSIDES FOR CONTROLLED DRUG RELEASE

BACKGROUND OF THE INVENTION

1. Field of the Invention

The present invention relates to an improved spherical-like encapsulated aminoglycoside, specifically gentamicin, formed by means of a two-phase system, and to a method for preparing such a spherical-like encapsulated product. The present invention also provides a method for introducing gentamicin into a patient orally without significant degradation of the gentamicin stomachically.

2. Description of the Prior Art

The aminoglycosides are composed of aminosugars connected to a central hexose by glycosidic linkage. Most aminoglycosides are prepared by natural fermentation from various species of Streptomyces, or in the case of gentamicin, from Micromonspora. In general, aminoglycosides have similar antibacterial spectra and pharmacokinetic properties. The drugs contain one or two aminosugars glycosidally linked to an aminocyclitol nucleus and are more accurately termed aminoglycosidic aminocyclitols. The aminocyclitol nucleus of gentamicin and the closer related drugs such as kanamycin, neomycin etc. is true dioxystreptomycin.

Although the invention is directed to the aminoglycosides generally, the member of this group that is of most interest is gentamicin. Gentamicin is an aminoglycoside antibacteric indicated in the treatment of several gram-negative infections, primarily pseudomonas infections, including complicated urinary tract infections, bacteremia and intra-abdominal infections. The drug has proved useful in serious infections in burned patients, respiratory tract infections, endophtalmitis, osteomyelitis, Serratia infections, antibiotic-resistant meningitis and severe diarrhea in infants.

Under aerobic conditions, the aminoglycosides are bactericidal, but their exact mechanism of action is unknown. They must be actively transported into susceptible bacteria. Based on the studies of Pratt, done primarily with streptomycin in 1977, the aminglycosides bind to the bacterial 30S ribosomal subunit to produce a nonfunctional 70S initiation complex that, in turn, results in the inhibition of bacterial cell protein synthesis and misreading of the genetic code. All of the aminoglycosides bind to the 30S subunit, and most of them appear to have additional interactions with this subunit when compared to streptomycin.

It is not known why the aminoglycosides are bactericidal, while other antibiotics such as the tetracyclines, for example, that impair protein synthesis are usually only bacteriostatic. Bacterial cell death does not appear to correlate with the production of faulty proteins due to the misreading of the genetic code. Pratt in his 1977 work suggested the lethal effect of the animoglycosides may result from their high affinity for the 30S subunit that leads to irreversible binding, but other mechanisms, such as effects on bacterial membranes, also may be involved.

U.S. Pat. No. 3,136,704 to Charney describes a method for production of gentamicin by a gentamicin producing strain of micromonospora in aqueous nutrient medium under aerobic consitions.

U.S. Pat. No. 3,091,572 to Luedemann et al describes a method of preparing gentamicin by cultivation under controlled conditions of a species of the genus micromonospora of the order actinomycetales.

Heretofore, gentamicin has not been effectively administered orally and correspondingly has been given by intermittent intravenous injection, intravenous infusion, or deep subcutaneous injection. The intramuscular route of administration has been avoided because of the frequent occurrence of hematoma at the injection site. In addition, intramuscular injection of gentamicin frequently causes local irritation, and pain.

Saffran et al. disclose in *Science* Vol. 223, pages 1081–1084 (1986), that oral administration of certain peptide drugs is well known to be precluded by their digestion in the stomach and small intestine. As a new approach to oral delivery, they propose to coat the peptide hormones vasopressin and insulin with polymers cross-linked with azoarmatic groups to form an impervious film, which protects these drugs, when orally administered, from digestion in the stomach and small intestine. When these polymer-coated drugs reach the large intestine, the indigenous microflora reduce the azo bonds, break the cross-links, and degrade the polymer film, thereby causing release of either the coated peptide hormones, vasopressin or insulin, into the lumen of the colon for local action, or for absorption.

It is readily apparent that the prior art has provided a number of approaches for preparing compounds which introduce drugs into a patient. However, none of these prior art attempts has been successfully applied to oral administration of gentamicin.

These and other defects and disadvantages, of the prior art practice of administering gentamicin into a patient, are now overcome by practice of the present invention.

SUMMARY OF THE INVENTION

The above disadvantages of the prior art are overcome by practice of the present invention whereby gentamicin is introduced into a patient orally, and without significant degradation stomachically, by means of a spherical-like encapsulated system.

It is an object of this invention to provide a method for preparing spherical-like encapsulated gentamicin, as well as to the resultant product.

It is also an object of this invention to provide spherical-like encapsulated gentamicin which may be consumed by a patient orally, and which retains antibiotic properties without significant degradation stomachically.

It is yet another object of this invention to provide a method for introducing gentamicin into a patient by ingesting orally spherical-like encapsulated gentamicin.

It is yet another object of this invention to provide a new improved drug dosage form of gentamicin which may be more controllably introduced by oral administration.

These and other objects and advantages will become more apparent from the following detailed description of the present invention.

It is understood that practice of the present invention may be applied to aminoglycosides generally as well as gentamicin.

Gentamicin is a white amorphous powder, with a melting point of 102°–108° C., which is freely soluble in water and forms a salt in acid media.

Aminoglycosides generally, and gentamicin specifically, are commercially available as sulfate salts which are sparingly soluble to freely soluble in water and insoluble in alcohol. The drugs are highly polar molecules and are relatively lipid insoluble.

In order for gentamicin to be successfully formulated for oral administration, it is necessary to demonstrate that gentamicin will be absorbed, after passing the intestinal mucosal barrier, to provide an efficiency of absorption in the range of about 20% to about 100%, with about 30% to about 70% being sufficient for practical application. Once having entered the portal circulation from the small intestine, the presently prepared gentamicin is released in a manner demonstrating a useful pharmacokinetic profile, and without significant toxicity. Thus, gentamicin formulated by practice of the present invention is absorbed, and released effectively, following oral administration, while remaining in a biologically active form having significant bactericidal activity.

Practice of the present invention will become more apparent from the following detailed description of the preferred embodiment.

DETAILED DESCRIPTION OF THE PREFERRED EMBODIMENT

The present invention encompasses the concept of encapsulating aminoglycosides, and more specifically gentamicin, as a spherical-like formation by dissolving a phospholipid in water, adding an alcohol to the dissolved phospholipid to cause the phospholipid-water solution to separate into three immiscible phases, separating the middle phase from the other two phases, adding a surface active protein to the middle phase, storing the mass under refrigeration until the solution separates into a relatively semi-polar to a non-polar colloid rich phase, and a relatively semi-polar to a polar colloid poor phase, and combining gentamicin with the colloid poor phase. Thus, a two phase liquid system is formed consisting of a non-polar phase insoluble in, and in equilibrium with, a polar liquid aqueous phase. Gentamicin in the colloid poor phase is recovered for administration, the remaining phases being either discarded, or used to prepare additional encapsulated gentamicin.

The internal phase comprises about 10% by weight of the two phase system. The external phase makes up correspondingly about 50% to about 90% by weight of the aqueous liquid system. The two phase system herein described can be prepared by dispersing from about 5%, by weight, to about 15%, by weight, of albumin in distilled water, containing about 1% to about 5%, by weight, urea, and subsequently adding from about 0.1% to about 10% by weight, of a surface active agent such as lecithin. Lecithin is a preferred surface active agent although any of the following phospholipids, or mixtures thereof, may be used as a substitute for lecithin. These phospholipids include cephalin, isolecthin, sphingomyelin, phosphatidyl serine, phosphatidic acid, phosphatidyl inositol and phosphatidyl choline, and the like. Other similar compounds, known to the art, may also be used.

An alternative method for preparing the two phase system is by combining a gelatin solution and acacia USP with distilled water. The resulting solution is then adjusted, depending upon the desired effect, to a pH in the range of about 6 to about 9 by using either sodium hydroxide or sodium bicarbonate.

The methods of preparation of the two phase system may be one of several. In practice, the underlying requirement is that any ingredient, or combination of ingredients, must be capable of forming a nontoxic two phase aqueous solution. Further, the mode of preparation results in a two phase aqueous system having an external equilibrium phase and an internal suspension phase. Although the two phases have similar molecules, the concentration of the component molecules will be different in each of the two phases.

At this point gentamicin may be added and the two phases may be separated. Alternatively, upon separation of the two phases, gentamicin is added to the recovered internal suspension phase. Gentamicin may be added in an amount of about 0.005%, by weight, to about 10%, by weight, and preferably in an amount from about 0.1% to about 4.5%, by weight.

In preparing the present composition, the internal phase is structured as water insoluble aqueous droplets which can coalesce. Thus, this layer can be readily emulsified to form droplets of any desired size, such as in the range of about one to about seven microns in diameter, containing gentamicin. For oral administration, the recovered gentamicin within the internal phase may be processed into a gelatin capsule or may be dried and processed as a tablet, layered onto a pill, or other means suitable for oral administration.

In order to more fully explain the present invention, the following general examples of the method of preparation are given. All parts are given by weight, unless indicated otherwise.

EXAMPLE 1

In this example, the steps involving refrigeration take place at 10 degrees C. All other steps are carried out at 25 degrees C. Twenty five grams of albumin is added to 500 mls. of distilled water containing 3%, by weight, of urea. The resulting solution is then thoroughly mixed, placed in an appropriate glass container, sealed and left undisturbed in a refrigerator for twelve hours. 500 mls. of a 2.5% solution of lecithin is then added. The solution is placed in a 2 liter flat bottom flask and thoroughly mixed. The flask is again sealed and refrigerated for seven days. After this period of time, the solution is adjusted to a pH of about 7 to about 7.5, using sodium bicarbonate. The solution is agitated for one hour and then stored, undisturbed in a refrigerator at a temperature of 10 degrees C., for seven days. At the end of this period, the solution separates into two layers, the bottom layer which consists of an internal aqueous phase, and the top layer which constitutes the equilibrium water phase. The phases are separated in a conventional manner. Into the internal aqueous phase is then added 2 grams of gentamicin. Then the internal aqueous phase is emulsified to give a suspension of globules containing gentamicin in the range of from about 1 to about 7 microns. The resultant emulsion can then be stored or introduced as a drug orally into a patient.

Obviously many modifications and variations of the invention may be made without departing from the essence and scope thereof. Only such limitations should be applied as are listed in the appended claims.

What is claimed is:

1. A method for preparing substantially spherical encapsulated gentamicin which comprises:

(a) dissolving a phospholipid in water;

(b) adding alcohol, thereby causing the dissolved phospholipid-water solution to separate into three immiscible phases, namely an upper, middle and lower phase;

(c) separating the middle phase from the other two phases;
(d) adding a surface active agent to the middle phase;
(e) storing the mass of step (d) under refrigeration until the solution separates into a relatively semi-polar to a non-polar colloid rich phase, and a relatively semi-polar to a polar colloid poor phase;
(f) combining gentamicin with the colloid poor phase to form substantially spherical encapsulated gentamicin; and
(g) recovering the encapsulated gentamicin.

2. The method of claim 1 wherein albumin is present in the water in an amount of about 5% to about 15%, by weight, the water additionally contains about 1% to about 5%, by weight, of urea added in an amount that will result in about a 5%, by weight, albumin solution;
wherein the surface active agent is lecithin present in an amount from about 0.1%, by weight, to about 10%, by weight;
wherein the storing the mass of step (d) further comprises storing the mass until two distinct layers form, the lower layer comprising an internal suspension phase, the upper layer constituting an external suspension phase, said internal suspension phase constituting about 10% to about 50%, by weight, of the system;
and wherein the gentamicin is present in an amount of about 0.005%, by weight, to about 10%, by weight.

3. A composition comprising:
substantially spherical encapsulated gentamicin and a surface active agent prepared by the method of claim 1 or 2.

4. A method for preparing substantially spherical encapsulated aminoglycosides which comprises:
(a) dissolving a phospholipid in water;
(b) adding alcohol, thereby causing the dissolved phospholipid-water solution to separate into three immiscible phases, namely an upper, middle and lower phase;
(c) separating the middle phase from the other two phases;
(d) adding a surface active agent to the middle phase;
(e) storing the mass of step (d) under refrigeration until the solution separates into a relatively semi-polar to a non-polar colloid rich phase, and a relatively semi-polar to a polar colloid poor phase;
(f) combining an aminoglycoside with the colloid poor phase to form substantially spherical encapsulated aminoglycosides; and
(g) recovering the encapsulated aminoglycosides.

5. The method of claim 4 wherein albumin is present in the water in an amount of about 5% to about 15%, by weight, the water additionally contains about 1% to about 5%, by weight, of urea added in an amount that will result in about a 5%, by weight, albumin solution;
wherein the surface active agent is lecithin present in an amount from about 0.1%, by weight, to about 10%, by weight;
wherein the storing the mass of step (d) further comprises storing the mass until two distinct layers form, the lower layer comprising an internal suspension phase, the upper layer constituting an external suspension phase, said internal suspension phase constituting about 10% to about 50%, by weight, of the system;
and wherein the aminoglycoside is present in an amount of about 0.005%, by weight, to about 10%, by weight.

* * * * *